US012729173B2

(12) United States Patent
Kajanto

(10) Patent No.: US 12,729,173 B2
(45) Date of Patent: Sep. 8, 2026

(54) RECOVERING MONO-ETHYLENE GLYCOL

(71) Applicants: The Coca-Cola Company, Atlanta, GA (US); Changchun Meihe Science and Technology Development Co., Ltd., Changchun (CN)

(72) Inventor: Isko Kajanto, Espoo (FI)

(73) Assignees: The Coca-Cola Company, Atlanta, GA (US); Changchun Meihe Science and Technology Development Co., Ltd., Changchun (CN)

( * ) Notice: Subject to any disclaimer, the term of this patent is extended or adjusted under 35 U.S.C. 154(b) by 162 days.

(21) Appl. No.: 18/556,146

(22) PCT Filed: Apr. 19, 2021

(86) PCT No.: PCT/FI2021/050286

§ 371 (c)(1),
(2) Date: Oct. 19, 2023

(87) PCT Pub. No.: WO2022/223867

PCT Pub. Date: Oct. 27, 2022

(65) Prior Publication Data

US 2024/0182391 A1 Jun. 6, 2024

(51) Int. Cl.
*B01D 3/32* (2006.01)
*B01D 3/36* (2006.01)
(Continued)

(52) U.S. Cl.
CPC .............. *C07C 29/82* (2013.01); *B01D 3/322* (2013.01); *B01D 3/36* (2013.01); *B01D 3/4205* (2013.01)

(58) Field of Classification Search
CPC ........ B01D 3/322; B01D 3/36; B01D 3/4205; C07C 29/82
See application file for complete search history.

(56) References Cited

U.S. PATENT DOCUMENTS 5,340,446 A * 8/1994 Nelson ................. C07D 301/32 203/91
10,035,744 B2 * 7/2018 Huizenga ........... B01D 11/0492
(Continued)

FOREIGN PATENT DOCUMENTS

CN 110357763 10/2019
CN 110357763 A * 10/2019 ............ C07C 29/84
(Continued)

OTHER PUBLICATIONS

International Search Report for PCT/FI2021/050286, issued Jan. 27, 2022.

*Primary Examiner* — Jonathan Miller
(74) *Attorney, Agent, or Firm* — King & Spalding

(57) ABSTRACT

A method for recovering mono-ethylene glycol from a mixture feed comprising bio-derived diols is disclosed. The mixture feed comprises mono-ethylene glycol in an amount of at least 80 weight-% of the total weight of the mixture feed. The method comprises: —providing the mixture feed into a distillation column, wherein a distillation process is carried out, wherein the distillation column comprises at least 80 theoretical stages and wherein the mixture feed is fed into the distillation column at a point, which is at a height of 5-20% of the total height of the distillation column as calculated from the top of the distillation column, wherein the total height of the distillation column is determined based on the number of theoretical stages, and wherein the distillation process is carried out with a reflux ratio of 20-200; and —recovering mono-ethylene glycol. Further is disclosed a distillation arrangement.

15 Claims, 1 Drawing Sheet

(51) Int. Cl.

| | |
|---|---|
| ***B01D 3/42*** | (2006.01) |
| ***C07C 29/82*** | (2006.01) |

(56) References Cited

U.S. PATENT DOCUMENTS

| | | | | |
|---|---|---|---|---|
| 10,266,470 | B2 * | 4/2019 | Huizenga | C07C 29/80 |
| 11,203,561 | B2 * | 12/2021 | Huizenga | B01D 3/42 |
| 2013/0284584 | A1 * | 10/2013 | Xiao | C07C 29/82<br>203/68 |
| 2018/0079702 | A1 * | 3/2018 | Huizenga | C07C 29/82 |
| 2019/0062244 | A1 * | 2/2019 | Perez Golf | C07C 29/84 |
| 2020/0377438 | A1 * | 12/2020 | Huizenga | B01D 3/42 |

FOREIGN PATENT DOCUMENTS

| | | |
|---|---|---|
| CN | 112079688 | 12/2020 |
| JP | 2009013094 | 1/2009 |
| WO | WO 2020/048444 | 3/2020 |

* cited by examiner

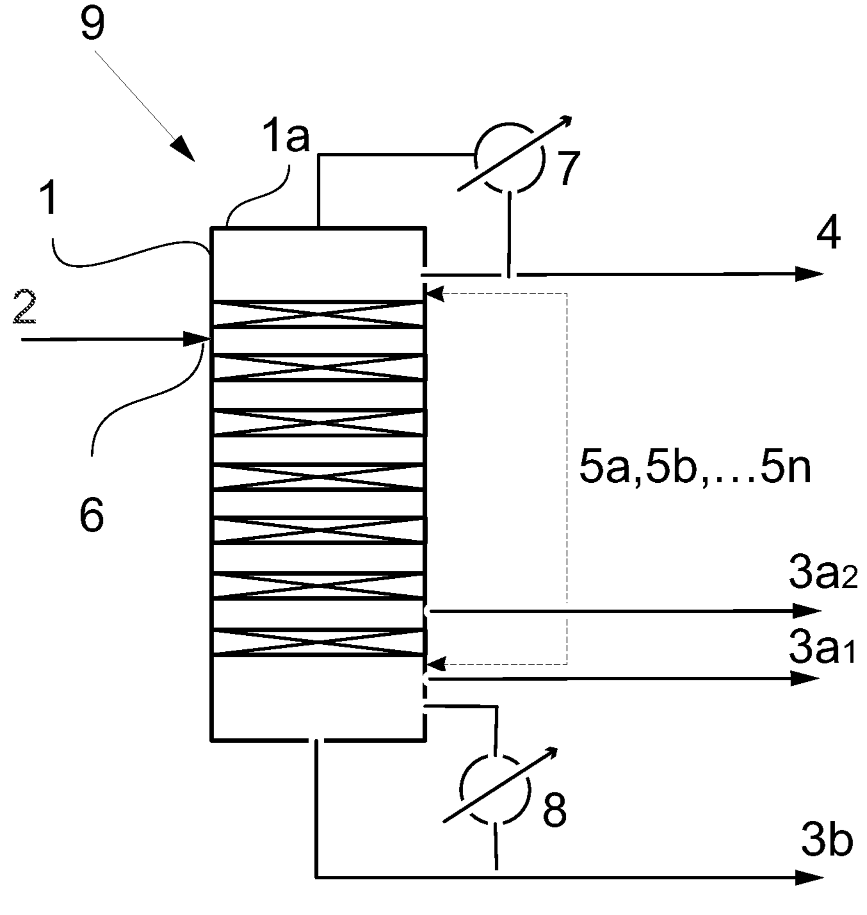
9
1a
7
1
4
2
6
5a,5b,…5n
3a2
3a1
8
3b

RECOVERING MONO-ETHYLENE GLYCOL

RELATED APPLICATIONS

The present application is a 371 national phase application of PCT/FI2021/050286 filed Apr. 19, 2021. The entire content of the foregoing application is incorporated herein by reference.

TECHNICAL FIELD

The present disclosure relates to a method for recovering mono-ethylene glycol from a mixture feed comprising bio-derived diols. The present disclosure further relates to a distillation arrangement for recovering mono-ethylene glycol from a mixture feed comprising bio-derived diols.

BACKGROUND

Mono-ethylene glycol, also called ethylene glycol or ethane-1,2-diol, is an organic compound with the formula $(CH_2OH)_2$. Mono-ethylene glycol may be used e.g. as a raw material in the manufacture of polyester fibers and for antifreeze formulations. Mono-ethylene glycol is an odorless, colorless, sweet-tasting, viscous liquid.

Mono-ethylene glycol may be produced from sugars together with other diols such as mono-propylene glycol. However, when producing such polyols as mono-ethylene glycol and mono-propylene glycol from sugars also other diols, alcohols and other substances are formed as side-products. In purification of biomass-based mono-ethylene glycol challenges may be faced with the fact that during the production process, different reactions produce also these other diols than mono-ethylene glycol that have a boiling point close to the one of mono-ethylene glycol. An example of such a substance is 1,2-butanediol, having a boiling point that is almost the same as the boiling point of mono-ethylene glycol. The inventor has thus recognized the need to provide a manner for recovering purified mono-ethylene glycol.

SUMMARY

A method for recovering mono-ethylene glycol from a mixture feed comprising bio-derived diols is disclosed. The mixture feed comprises mono-ethylene glycol in an amount of at least 80 weight-% of the total weight of the mixture feed. The method comprises: —providing the mixture feed into a distillation column, wherein a distillation process is carried out, wherein the distillation column comprises at least 80 theoretical stages and wherein the mixture feed is fed into the distillation column at a point, which is at a height of 5-20% of the total height of the distillation column as calculated from the top of the distillation column, wherein the total height of the distillation column is determined based on the number of theoretical stages, and wherein the distillation process is carried out with a reflux ratio of 20-200; and —recovering mono-ethylene glycol.

Further is disclosed a distillation arrangement for recovering mono-ethylene glycol from a mixture feed comprising bio-derived diols. The mixture feed comprises mono-ethylene glycol in an amount of at least 80 weight-% of the total weight of the mixture feed. The distillation arrangement comprises:

- a distillation column comprising at least 80 theoretical stages, and wherein the distillation column is configured to operate with a reflux ratio of 20-200;
- an inlet for providing the mixture feed into the distillation column, wherein a distillation process is carried out, wherein the inlet is situated at a point, which is at a height of 5-20% of the total height of the distillation column as calculated from the top of the distillation column, wherein the total height of the distillation column is determined based on the number of theoretical stages; and
- an outlet for recovering mono-ethylene glycol.

BRIEF DESCRIPTION OF THE DRAWINGS

The accompanying drawing, which is included to provide a further understanding of the embodiments and constitutes a part of this specification, illustrates an embodiment. In the drawing:

FIG. 1 discloses one embodiment of the distillation arrangement disclosed in the current specification.

DETAILED DESCRIPTION

A method for recovering mono-ethylene glycol from a mixture feed comprising bio-derived diols is disclosed. The mixture feed comprises mono-ethylene glycol in an amount of at least 80 weight-% of the total weight of the mixture feed. The method comprises: —providing the mixture feed into a distillation column, wherein a distillation process is carried out, wherein the distillation column comprises at least 80 theoretical stages and wherein the mixture feed is fed into the distillation column at a point, which is at a height of 5-20% of the total height of the distillation column as calculated from the top of the distillation column, wherein the total height of the distillation column is determined based on the number of theoretical stages, and wherein the distillation process is carried out with a reflux ratio of 20-200; and —recovering monoethylene glycol.

Further is disclosed a distillation arrangement for recovering mono-ethylene glycol from a mixture feed comprising bio-derived diols. The mixture feed comprises mono-ethylene glycol in an amount of at least 80 weight-% of the total weight of the mixture feed. The distillation arrangement comprises:

- a distillation column comprising at least 80 theoretical stages, and wherein the distillation column is configured to operate with a reflux ratio of 20-200;
- an inlet for providing the mixture feed into the distillation column, wherein a distillation process is carried out, wherein the inlet is situated at a point, which is at a height of 5-20% of the total height of the distillation column as calculated from the top of the distillation column, wherein the total height of the distillation column is determined based on the number of theoretical stages; and
- an outlet for recovering mono-ethylene glycol.

Distillation may generally be considered a process of separating components or substances from a mixture by using selective boiling and condensation. Distillation may result in essentially complete separation into nearly pure components, or it may be a partial separation that increases the concentration of selected components in the mixture. The distillation process exploits differences in the relative volatility of the different components in the mixture.

A “theoretical stage”, a “theoretical plate” or a “distillation stage” as it may also be called, that may be used in many separation processes can be considered as a hypothetical zone or stage in which two phases, such as the liquid and vapor phases of a substance, establish an equilibrium with each other. Such equilibrium stages may also be referred to as an equilibrium stage, ideal stage, or a theoretical tray. The performance of many separation processes depends on having series of equilibrium stages and may be enhanced by providing more such stages. In other words, having more theoretical plates increases the efficiency of the separation process be it either a distillation, absorption, chromatographic, adsorption or similar process.

When designing the distillation of a certain media, the number of theoretical stages is usually first designed or considered and the theoretical stages then define the physical height of the distillation column. In the distillation column the theoretical stages or distillation stages may be formed by trays or packings, also called packed beds. A packed bed may be a structured packed bed or a random packed bed.

The inventor surprisingly found out that the combination of using the specified number of theoretical stages and the specified reflux ratio enabled an efficient separation of the mono-ethylene glycol in a high purity or yield from the mixture feed comprising bio-derived diols. The combination of the specified number of theoretical stages and the specified reflux ratio has the added utility of allowing to feed the mixture feed into the distillation column at a high that beneficially assist in recovering mono-ethylene glycol in high purity.

The mixture feed comprising bio-derived diols may comprise e.g. mono-ethylene glycol (MEG, also called ethylene glycol or 1,2-ethanediol), mono-propylene glycol (MPG, also called 1,2-propanediol), and butylene glycol (BDO, also called butanediol). Such a mixture feed of bio-based diols may be derived e.g. from a process for the production of glycols, such as a process for producing mono-ethylene glycol. In one embodiment, the mixture feed comprising bio-derived diols comprises mono-ethylene glycol, mono-propylene glycol, and butylene glycols. Butylene glycol may appear in structures differing from each other in where the OH-units are situated. Such structures are e.g. 1,2-butanediol, 2,3-butanediol, and 1,4-butanediol. These have different boiling points. 2,3-butanediol has a lower boiling point than mono-ethylene glycol, 1,2-butanediol has almost the same boiling point as mono-ethylene, and 1,4-butanediol has a boiling point that is higher than the boiling point of mono-ethylene glycol.

The mixture feed may comprise mono-ethylene glycol in an amount of at least 85 weight-%, or at least 87 weight-%, of the total weight of the mixture feed. The mixture feed may comprise mono-ethylene glycol, mono-propylene glycol, and butylene glycol, in an amount of at least 90 weight-%, or at least 95 weight-%, or at least 97 weight-%, or at least 99 weight-%, of the total weight of the mixture feed.

The mixture feed comprising bio-derived diols may further comprise water. In one embodiment, the mixture feed comprises water in an amount of 0-2 weight-%, or 0.5-1.5 weight-%, based on the total weight of the mixture feed. In one embodiment, the mixture feed comprises essentially no water.

The mixture feed may be fed into the distillation column in the form of a liquid or as a steam or vapor.

Mono-ethylene glycol as well as mono-propylene glycol may be produced from a process to prepare a liquid composition of glycols comprising e.g. mono-ethylene glycol. Such a liquid composition of glycols may be prepared from plant-based raw material. The plant-based raw material may be wood-based raw material, such as from hardwood or softwood. The wood-based raw material may originate from e.g. pine, poplar, beech, aspen, spruce, eucalyptus, ash, oak, maple, chestnut, willow, or birch. The wood-based raw material may also be any combination or mixture of these.

Such a method for producing a liquid composition of glycols may comprise:

- providing a wood-based feedstock originating from wood-based raw material and comprising wood chips, and subjecting the wood-based feedstock to at least one pretreatment to form a liquid fraction and a fraction comprising solid cellulose particles;
- subjecting the fraction comprising solid cellulose particles to enzymatic hydrolysis to form a lignin fraction and a carbohydrate fraction;
- subjecting the carbohydrate fraction to catalytical conversion to form a liquid composition of glycols.

Providing the wood-based feedstock may comprise subjecting wood-based raw material to a mechanical treatment selected from debarking, chipping, dividing, cutting, beating, grinding, crushing, splitting, screening, and/or washing the wood-based raw material to form the wood-based feedstock. Providing the wood-based feedstock may comprise purchasing the wood-based feedstock.

Pretreatment of the wood-based feedstock may comprise at least one of the following: pre-steaming of the wood-based feedstock, subjecting the wood-based feedstock to an impregnation treatment, and subjecting the wood-based feedstock to steam explosion.

The pretreatment may comprise subjecting the wood-based feedstock to pre-steaming. The pretreatment may comprise, an impregnation treatment and/or a steam explosion and may comprise, before subjecting the wood-based feedstock to impregnation treatment and/or to steam explosion, subjecting the wood-based feedstock to pre-steaming. The pre-steaming of the wood-based feedstock may be carried out with steam having a temperature of 100-130° C. at atmospheric pressure. During the pre-steaming the wood-based feedstock is treated with steam of low pressure. The pre-steaming may be also carried out with steam having a temperature of below 100° C., or below 98° C., or below 95° C.

Further, the pretreatment may comprise subjecting the wood-based feedstock to at least one impregnation treatment with an impregnation liquid. The impregnation treatment may be carried out to the wood-based feedstock received from the mechanical treatment and/or from the pre-steaming. The pretreatment may comprise, before subjecting to the steam explosion, subjecting the wood-based feedstock to at least one impregnation treatment with an impregnation liquid selected from water, at least one acid, at least one alkali, at least one alcohol, or any combination or mixture thereof. The impregnation liquid may comprise water, at least one acid, at least one alkali, at least one alcohol, or any combination or mixture thereof.

The pretreatment may comprise subjecting the wood-based feedstock to steam explosion. The wood-based feedstock from the mechanical treatment, the pre-steaming step, and/or from the impregnation treatment may be subjected to steam explosion.

The pretreatment may comprise at least one of mechanical treatment of wood-based material to form wood-based feedstock, pre-steaming of the wood-based feedstock, impregnation treatment of the wood-based feedstock, and steam explosion of the wood-based feedstock. The pretreatment may comprise mechanical treatment of wood-based material to form a wood-based feedstock, pre-steaming of the wood-based feedstock, impregnation treatment of the pre-steamed wood-based feedstock, and steam explosion of the impregnated wood-based feedstock. The pretreatment may comprise pre-steaming the wood-based feedstock, impregnation treatment of the pre-steamed wood-based feedstock, and steam explosion of the impregnated wood-based feedstock. The pretreatment may comprise impregnation treatment of the wood-based feedstock, and steam explosion of the impregnated wood-based feedstock. I.e. the wood-based feedstock having been subjected to the impregnation treatment may thereafter be subjected to the steam explosion. Also, the wood-based feedstock having been subjected to pre-steaming, may then be subjected to the impregnation treatment and thereafter the wood-based feedstock having been subjected to the impregnation treatment may be subjected to steam explosion.

In this specification, the term "steam explosion" may refer to a process of hemihydrolysis in which the wood-based feedstock is treated in a reactor with steam having a temperature of 130-240° C. under a pressure of 0.17-3.25 MPaG followed by a sudden, explosive decompression of the steam-treated wood-based feedstock that results in the rupture of the fiber structure. The output from the steam explosion may be mixed with a suitable liquid, e.g. water, to form a slurry comprising solid cellulose particles. The fraction comprising solid cellulose particles may be separated from the liquid fraction by a suitable separation method, e.g. by a solid-liquid separation.

The enzymatic hydrolysis of the fraction comprising solid cellulose particles may be carried out at a temperature of 30-70° C., or 35-65° C., or 40-60° C., or 45-55° C., or 48-53° C. while keeping the pH of the fraction comprising solid cellulose particles at a pH value of 3.5-6.5, or 4.0-6.0, or 4.5-5.5, and wherein the enzymatic hydrolysis is allowed to continue for 20-120 h, or 30-90 h, or 40-80 h. Enzymatic hydrolysis may result in the formation of a lignin fraction and a carbohydrate fraction. The enzymes are catalysts for the enzymatic hydrolysis. The enzymatic reaction decreases the pH and by shortening the length of the cellulose fibers it may also decrease the viscosity. Subjecting the fraction comprising solid cellulose particles to enzymatic hydrolysis may result in cellulose being transformed into glucose monomers with enzymes. Lignin present in the fraction comprising solid cellulose particles may remain essentially in solid form.

At least one enzyme may be used for carrying out the enzymatic hydrolysis. The at least one enzyme may be selected from a group consisting of cellulases, hemicellulases, laccases, and lignolytic peroxidases. Cellulases are multi-protein complexes consisting of synergistic enzymes with different specific activities that can be divided into exo- and endo-cellulases (glucanase) and β-glucosidase (cellobiose). The enzymes may be either commercially available cellulase mixes or on-site manufactured.

Catalytical conversion of the carbohydrate fraction may comprise subjecting the carbohydrate fraction to catalytical hydrogenolysis. I.e. the carbohydrate fraction may be subjected to catalysts in the presence of hydrogen. The catalytical conversion may be carried out in the presence of water. In one embodiment, the catalytical conversion of the carbohydrate fraction comprises subjecting the carbohydrate fraction to catalytical hydrogenation in the presence of a solvent, preferably water and a catalyst system. The catalytical conversion may be carried out in the presence of a catalyst system comprising one or more catalysts. The catalytical conversion may alternatively be carried out to a carbohydrate feed derived from sugar cane, sugar beet, corn and/or wheat.

Subjecting the carbohydrate fraction to catalytical conversion may result in a liquid composition of glycols. The catalytical conversion accomplishes at least hydrogenolation and hydrocracking reactions to achieve hydrogenolation and hydrocracking of the carbohydrate fraction such that a liquid composition of glycols is formed. The liquid composition of glycols may comprise or consist of mono-ethylene glycol, mono-propylene glycol and butylene glycol. These glycols may be present at a concentration of 0.1-40 weight-% based on the total weight of the liquid composition of glycols. The liquid composition of glycols may also comprise other side products. The liquid composition may also comprise water.

E.g. mono-ethylene glycol may be recovered from the liquid composition of glycols e.g. by a separation technique selected form adsorption, evaporation, distillation, extractive distillation, azeotrope distillation, vacuum distillation, atmospheric distillation, membrane separation, filtration, reactive purification or a combination of them.

The mixture feed comprising bio-derived diols applied in the current specification may however also be provided from any other process for the production of glycols. The method as described in the current specification should not be understood to be bound to the above described process for producing a liquid composition of glycols.

Prior to the distillation process described in the current specification there may be one or more separation or purification processes taking place. E.g. water, alcohols such as methanol and ethanol, organic acids, sugar alcohols such as glycerol, catalysts and residual sugars may be removed in separate steps in a desired order. Typically water and alcohols having the lowest boiling point may be removed first, followed by removing components having a boiling point higher than mono-ethylene glycol. The remaining components may comprise mainly diols with boiling points close to the one of mono-ethylene glycol which may then be separated in further purification steps.

By the expression "mixture feed comprising bio-derived diols" should be understood in this specification, unless otherwise stated, as a mixture feed of one or more diols, which are derived from a bio-based origin or raw material. In one embodiment, the bio-derived diols are plant-derived diols, e.g. wood-derived diols. The diols may thus be derived from e.g. hardwood, softwood, or from a combination of these. The diols may also be derived from broadleaf wood. The diols may be derived e.g. from pine, poplar, beech, aspen, spruce, eucalyptus, ash, or birch, or from any combination or mixture of these. The diols may further be derived from sugar cane, sugar beet, corn, wheat, or from any combination or mixture of these.

The method as described in the current specification has the added utility of enabling to separate mono-ethylene glycol in a high purity from a mixture feed comprising also other diols that have a boiling point close to mono-ethylene glycol. An example of such a substance is 1,2-butanediol having almost the same boiling point as mono-ethylene glycol. Mono-ethylene glycol and 1,2-butanediol also form an azeotrope having a lower boiling point than mono-ethylene glycol and that can then be separated from mono-ethylene glycol. Thus, some loss of mono-ethylene glycol in the azeotrope may thus occur during the distillation process. However, the molar ratio of mono-ethylene glycol and 1,2-butanediol in the azeotrope is about 50:50, such as 45:55. Thus, even if some mono-ethylene glycol is lost with the azeotrope, the amount of lost mono-ethylene glycol is rather low as a result of the favourable molar ratio.

An azeotrope may be considered to be a mixture that exhibits the same concentration in the vapor phase and the liquid phase. This is in contrast to ideal solutions with one component typically more volatile than the other. If the mixture forms an azeotrope, the vapor and the liquid concentrations are the same, which may prevent separation via this approach.

The distillation process as disclosed in the current specification is carried out in a distillation column. In one embodiment, the distillation column comprises at least 85, or at least 90, or at least 100, or at least 105, or at least 110, or at least 120, or at least 120, or at least 150, or at least 200, theoretical stages. The distillation column may comprise at most 1000, or at most 800, or at most 600, or at most 400 theoretical stages. The number of theoretical stages being at least 80 has the added utility of enabling separation to take place in rather high efficiency.

The mixture feed may be fed into the distillation column at a point, which is situated between two theoretical stages. However, the distillation column may comprise packings or packed beds, wherein one packed bed comprises two or more theoretical stages. In such a situation, the mixture feed may be fed into the distillation column at a point between two such packed beds. In one embodiment, the mixture feed is fed into the distillation column at a point, which is situated below at least one theoretical stage.

In one embodiment, the mixture feed is fed into the distillation column at a point, which is at a height of 7-18%, or 9-17%, or 12-16%, or 13-15%, or 14-16%, of the total height of the distillation column as calculated from the top of the distillation column. In one embodiment, the inlet is situated at a point, which is at a height of 7-18%, or 9-17%, or 12-16%, or 13-15%, or 14-16%, of the total height of the distillation column as calculated from the top of the distillation column.

In one embodiment, the distillation process is carried out with a reflux ratio of 25-150, or 30-100, or 35-80, or 40-50, or 35-45. In one embodiment, the distillation column is configured to operate with a reflux ratio of 25-150, or 30-100, or 35-80, or 40-50 or 35-45. The reflux ratio may generally be defined as the ratio of the top liquid returned to the distillation column divided by the liquid removed or recovered from the distillation column as product.

The inventor surprisingly found out that especially the combination of the point wherein the mixture feed is fed into the distillation column together with reflux ratio used has the added utility of enabling the recovering of mono-ethylene glycol with high purity and yield. In one embodiment, the method comprises recovering mono-ethylene glycol at a concentration of 96-99 weight-%, or 97-98 weight-%, or 96-97 weight-%. The yield is calculated as the percentage of the amount of recovered mono-ethylene glycol compared to the amount of mono-ethylene glycol in the mixture feed. In one embodiment, the mono-ethylene glycol is recovered with a purity of 99.3-99.99 weight-%, or 99.5-99.9 weight-%, or 99.6-99.8 weight-%. The purity is calculated as the percentage of the amount of mono-ethylene glycol in the recovered product compared to the total amount of recovered product flow.

In one embodiment, the distillation process is carried out at a top temperature of at most 160° C. and a top pressure of at most 0.4 bar. In one embodiment, the distillation process is carried out at a top temperature of at most 159° C., or at most 157° C., at most 155° C., or at most 155° C., or at most 150° C., or at most 145° C. In one embodiment, the distillation process is carried out at a top pressure of at most 0.35 bar, or at most 0.3 bar. In one embodiment, the distillation process is carried out at a top temperature of 50-160° C., or 65-155° C., or 75-150° C., or 100-145° C. In one embodiment, the distillation process is carried out at a top pressure of 0.1-0.4 bar, or 0.2-0.35 bar, or 0.25-0.3 bar.

In one embodiment, the distillation column is configured to operate at a top temperature of at most 160° C. and a top pressure of at most 0.4 bar. In one embodiment, the distillation column is configured to operate at a top temperature of at most 159° C., or at most 157° C., at most 155° C., or at most 155° C., or at most 150° C., or at most 145° C. In one embodiment, the distillation column is configured to operate at a top pressure of at most 0.35 bar, or at most 0.3 bar. In one embodiment, the distillation column is configured to operate at a top temperature of 50-160° C., or 65-155° C., or 75-150° C., or 100-145° C. In one embodiment, the distillation column is configured to operate at a top pressure of 0.1-0.4 bar, or 0.2-0.35 bar, or 0.25-0.3 bar.

In one embodiment, the pressure drop over the distillation column is 0.02-0.2 bar, or 0.05-0.12 bar.

The bottom temperature of the distillation column may be kept at a temperature of at most 170° C. Keeping the bottom temperature of the distillation column at a temperature of at most 170° C. has the added utility of hindering or reducing compound degradation to take place.

In this specification, the term "top temperature" is used to refer to the temperature at the vapor space in the distillation column that is above the topmost packed bed or stage and below the vapor pipe of the distillation column. It is clear to the person skilled in the art that the temperature in the distillation column as such may differ from the temperature in e.g. the condenser or the reboiler that may be operationally connected to the distillation column.

In this specification, the term "top pressure", is used to refer to the pressure at the vapor space in the distillation column that is above the topmost packed bed or stage and below the vapor pipe of the distillation column.

In one embodiment, at least one condenser is used in the distillation process. In one embodiment, the distillation arrangement comprises at least one condenser. I.e. one condenser or a series of at least two condensers may be used in the distillation process. If for example a series of two condensers is used, then the vapor fraction after the first condenser may be 5-20% %, e.g. about 15%, and the vapor fraction after the second condenser may be below 1%. The condenser (s) used may be (a) partial condenser (s), (a) total condenser (s) or a combination of these may be used. The condenser (s) may be heat integrated or they may use a cooling medium, such as cooling water, or they may function with air cooling.

In one embodiment, a reboiler is used in the distillation process. In one embodiment, the distillation arrangement comprises a reboiler. The reboiler may be operated at a vapor pressure of 0.1-0.5 bar, or 0.3-0.5 bar. In one embodiment, the distillation arrangement comprises a reboiler, wherein the reboiler is configured to operate at a pressure of 0.1-0.5 bar, or 0.3-0.5 bar.

The distillation process, or the distillation column, respectively, may be equipped with a heat integration, wherein heat recovered from the at least one condenser is led or transferred to the reboiler. I.e. the heat recovered from the at least one condenser may be reused in the reboiler.

In one embodiment, recovering mono-ethylene glycol comprises removing mono-ethylene glycol from the distillation column at a point, which is situated below the point, wherein the mixture feed is fed into the distillation column. In one embodiment, the outlet for recovering mono-ethylene glycol is situated at a point, which is situated below the point, wherein the inlet for feeding the mixture feed into the distillation column is situated.

Mono-ethylene glycol may be removed from the distillation column as a so-called side-draw or from the side of the distillation column. Mono-ethylene glycol may be removed from the distillation column as a side-draw below the lowest packed bed but above the bottom of the distillation column. Mono-ethylene glycol may be removed from the distillation column as a side-draw at a point below the point, wherein the inlet for feeding the mixture feed into the distillation column is situated but above the lowest packed bed. Alternatively or in addition mono-ethylene glycol may be removed from the distillation column in a bottom stream taken from the bottom of the distillation column.

In one embodiment, the point, wherein mono-ethylene glycol is removed from the distillation column, is situated below the lowest theoretical stage of the distillation column.

In one embodiment, the method comprises removing a top stream from the distillation column, wherein the top stream comprises mono-propylene glycol and an azeotrope of mono-ethylene glycol and 1,2-butylene glycol.

The method as described in the current specification has the added utility of enabling to separate mono-ethylene glycol in a high purity and a high yield from a mixture feed comprising also other diols that have a boiling point close to mono-ethylene glycol.

The method as described in the current specification has the added utility of being an economical process for recovering mono-ethylene glycol from the mixture feed.

EXAMPLES

Reference will now be made in detail to various embodiments.

The description below discloses some embodiments in such a detail that a person skilled in the art is able to utilize the embodiments based on the disclosure. Not all steps or features of the embodiments are discussed in detail, as many of the steps or features will be obvious for the person skilled in the art based on this specification.

For reasons of simplicity, item numbers will be maintained in the following exemplary embodiments in the case of repeating components.

The enclosed FIG. 1 discloses an example of an embodiment of the distillation arrangement 9 for recovering mono-ethylene glycol from a mixture feed comprising bio-derived diols. The mixture feed 2 comprises mono-ethylene glycol in an amount of at least 80 weight-% of the total weight of the mixture feed. Firstly the mixture feed is provided into a distillation column 1, wherein a distillation process is carried out. The distillation column comprises an inlet 2 for feeding the mixture feed into the distillation column. The distillation column 1 comprises packed beds comprising at least 80 theoretical stages 5*a*, 5*b*, . . . 5*n*. The mixture feed 2 is fed into the distillation column 1 at a point 6, which is at a height of 5-20% of the total height of the distillation column 1 as calculated from the top 1a of the distillation column. The total height of the distillation column is determined based on the number of theoretical stages 5*a*, 5*b*, . . . 5*n*. The distillation column is configured to operate with a reflux ratio of 20-200. Mono-ethylene glycol is recovered from the distillation column at a point (outlet) 3*a*1, 3*a*2, 3*b*, which is situated below the point 6, wherein the mixture feed is fed into the distillation column. FIG. 1 discloses the possibility of removing the mono-ethylene glycol through an outlet as a side-draw 3*a*1 and/or as a side-draw 3*a*2. In such a case, e.g. heavy compound impurities may be removed from the bottom of the distillation column. Alternatively, mono-ethylene glycol may be removed through an outlet as a bottom stream 3*b* from the bottom of the distillation column.

Example 1—Distillation of Mixtures Comprising Bio-Derived Diols

In this example, a mixture feed comprising bio-based diols was subjected to the distillation process.

The mixture feed comprised the following:

| | | |
|---|---|---|
| Mono-ethylene glycol (EG) | 8531 | kg/h |
| Mono-propylene glycol (PG) | 714 | kg/h |
| 1,2-butanediol (1,2-BDO) | 195 | kg/h |
| 2,3-butanediol (2,3-BDO) | 40 | kg/h |
| 1,2-hexanediol (1,2-HXD) | 14 | kg/h |

The separated products recovered or removed from the distillation column had the following composition and rates:

| | | |
|---|---|---|
| Mono-ethylene glycol (EG) | 8200 | kg/h |
| Bottom* | 15 | kg/h |
| Distillate** | 1279 | kg/h |

*bottom comprising heavy compound impurities
distillate comprises mono-propylene glycol, 1,2-butanediol, and 2,3-butanediol The distillation column was operated at a top temperature of 159° C., and a top pressure of 0.35 bar. Mono-ethylene glycol was removed as a side draw below the lowest theoretical stage (3*a*1 in FIG. 1**).

The reflux ratio as well as the number of theoretical stages were varied and the height of the point where the mixture feed was fed into the distillation column was determined. Based on the conducted tests it was noted that one is able to recover mono-ethylene glycol in a high yield and purity when keeping the above parameters withing the claimed ranges.

The yield of the mono-ethylene glycol in this example was 96 weight-%. Target purity was set at 99.8 weight-%, which is in the range of polymer grade ethylene glycol. This is near the theoretical maximum with the applied feed. The theoretical maximum purity is 99.83 weight-%.

The results are presented in the below table:

Table 1. Highest point, where mixture feed is fed into the distillation column calculated from the top of the distillation column, to reach 99.8 weight-% purity.

| Reflux | Theoretical stages | | | |
|---|---|---|---|---|
| ratio | 80 stages | 100 stages | 120 stages | 140 stages |
| 30 | | 14.0% | 10.8% | 9.3% |
| 35 | 16.3% | 11.0% | 9.2% | 7.9% |
| 40 | 11.3% | 9.0% | 7.5% | 6.4% |
| 45 | 11.3% | 9.0% | 5.8% | 5.0% |
| 50 | 8.8% | 7.0% | 5.8% | 5.0% |

In addition, the effect of the reflux ratio and the number of theoretical stages on the purity of the recovered mono-ethylene glycol was tested and measured. The results are presented in the below table:

TABLE 2

| Maximum purity reached | | | | |
|---|---|---|---|---|
| Reflux | Theoretical stages | | | |
| ratio | 80 stages | 100 stages | 120 stages | 140 stages |
| 25 | 99.65% | 99.73% | 99.77% | 99.79% |
| 30 | 99.79% | 99.83% | 99.83% | 99.83% |
| 35 | 99.82% | 99.83% | 99.83% | 99.83% |
| 40 | 99.83% | 99.83% | 99.83% | 99.83% |
| 45 | 99.83% | 99.83% | 99.83% | 99.83% |
| 50 | 99.83% | 99.83% | 99.83% | 99.83% |

As can be seen from the above table, when using 80 or more theoretical stages, the purity of the recovered mono-ethylene glycol increases. Table 2 shows the maximum purity reached with different combinations of theoretical stages and reflux ratio. From table 2, one can see that with most of the combinations of theoretical stages and reflux ratios the target purity 99.8 weight-% and even the maximum purity 99.83 weight-% was reached.

From table 1, one may see that the more theoretical stages were used and the higher the reflux ratio was, the higher in the distillation column is the point, where the mixture feed can be fed into the distillation column.

Example 2—Distillation of Mixtures Comprising Bio-Derived Diols and Water

In this example, the same mixture feed was applied as in example 1, with the exception that in this example, the mixture feed comprised an additional amount of water.

The mixture feed comprised the following:

| | | |
|---|---|---|
| Mono-ethylene glycol (EG) | 8531 | kg/h |
| Mono-propylene glycol (PG) | 714 | kg/h |
| 1,2-butanediol (1,2-BDO) | 195 | kg/h |
| 2,3-butanediol (2,3-BDO) | 40 | kg/h |
| 1,2-hexanediol (1,2-HXD) | 14 | kg/h |
| Water | 95 | kg/h |

The separated products recovered or removed from the distillation column had the following composition and rates:

| | | |
|---|---|---|
| Mono-ethylene glycol (EG) | 8300 | kg/h |
| Bottom* | 15 | kg/h |
| Distillate** | 1274 | kg/h |

*bottom comprising heavy compound impurities
distillate comprises mono-propylene glycol, 1,2-butanediol, and 2,3-butanediol The distillation column was operated at a top temperature of 151-152° C., and a top pressure of 0.35 bar. The temperature was lower at the same pressure compared to the temperature in example 1 as a result of the presence of water. Mono-ethylene glycol was removed as a side draw below the lowest theoretical stage (3*a*1 in FIG. 1**).

The reflux ratio as well as the number of theoretical stages were varied and the height of the point where the mixture feed was fed into the distillation column was determined. Based on the conducted tests it was noted that one is able to recover mono-ethylene glycol in a high yield and purity when keeping the above parameters withing the claimed ranges. A higher ethylene glycol flow was used compared to example 1 and the ethylene glycol yield was therefore higher at 97 weight-%. The results are presented in the below table:

TABLE 3

| Highest point, where mixture feed is fed into the distillation column calculated from the top of the distillation column, to reach 99.8 weight-% purity. | | | | |
|---|---|---|---|---|
| Reflux | Theoretical stages | | | |
| ratio | 80 stages | 100 stages | 120 stages | 140 stages |
| 20 | | | 20.0% | 15.0% |
| 25 | | 19.0% | 10.8% | 9.3% |
| 30 | 16.3% | 13.0% | 9.2% | 7.9% |
| 35 | 13.8% | 11.0% | 9.2% | 7.9% |
| 40 | 11.3% | 9.0% | 7.5% | 6.4% |

Also in this case the target purity was reached when feeding the mixture feed into the distillation column at a point, which is at a height of 5-20% of the total height of the distillation column as calculated from the top of the distillation column. Compared to example 1, these points were slightly lower in the distillation column.

The main effect of the presence of water in the mixture feed is the lower top temperature, and lower reflux rations. Since the reflux ratio is the reflux flow returned to the column divided by distillate flow, the reflux ratios decreased because the amount of water increases the reflux flow.

TABLE 4

| Maximum purity reached | | | | |
|---|---|---|---|---|
| Reflux | Theoretical stages | | | |
| ratio | 80 stages | 100 stages | 120 stages | 140 stages |
| 20 | 99.70% | 99.70% | 99.81% | 99.82% |
| 25 | 99.81% | 99.81% | 99.83% | 99.83% |
| 30 | 99.83% | 99.83% | 99.83% | 99.83% |
| 35 | 99.83% | 99.83% | 99.83% | 99.83% |
| 40 | 99.83% | 99.83% | 99.83% | 99.83% |

Table 4 shows that target purity was reached with most of the combinations of theoretical stages and reflux ratio.

It is obvious to a person skilled in the art that with the advancement of technology, the basic idea may be implemented in various ways. The embodiments are thus not limited to the examples described above; instead they may vary within the scope of the claims.

The embodiments described hereinbefore may be used in any combination with each other. Several of the embodiments may be combined together to form a further embodiment. A method and distillation arrangement disclosed herein, may comprise at least one of the embodiments described hereinbefore. It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item refers to one or more of those items. The term "comprising" is used in this specification to mean including the feature (s) or act (s) followed thereafter, without excluding the presence of one or more additional features or acts.

The invention claimed is:

1. A method for recovering mono-ethylene glycol from a mixture feed comprising bio-derived diols, wherein the mixture feed comprises mono-ethylene glycol in an amount of at least 80 weight % of the total weight of the mixture feed and wherein the mixture feed comprises mono-ethylene glycol, mono-propylene glycol, and butylene glycol, in an amount of at least 90 weight % of the total weight of the mixture feed, and wherein the method comprises:

(i) providing the mixture feed into a distillation column, wherein a distillation process is carried out, wherein the distillation column comprises at least 85 theoretical stages and wherein the mixture feed is fed into the distillation column at a point, which is at a height of 5-20% of the total height of the distillation column as calculated from the top of the distillation column, wherein the total height of the distillation column is determined based on the number of theoretical stages, and wherein the distillation process is carried out with a reflux ratio of 20-200, and wherein the distillation process is carried out at a top temperature of 50 to 160° C. and a top pressure of 0.1 to 0.4 bar; and (ii) recovering mono-ethylene glycol.

2. The method of claim 1, wherein the mixture feed comprises mono-ethylene glycol in an amount of at least 85 weight % of the total weight of the mixture feed.

3. The method of claim 1, wherein the mixture feed comprises mono-ethylene glycol, mono-propylene glycol, and butylene glycol, in an amount of at least 95 weight % of the total weight of the mixture feed.

4. The method of claim 1, wherein the distillation column comprises at least 90 theoretical stages.

5. The method of claim 1, wherein the mixture feed is fed into the distillation column at a point, which is at a height of 7-18% of the total height of the distillation column as calculated from the top of the distillation column.

6. The method of claim 1, wherein the distillation process is carried out with a reflux ratio of 25-150.

7. The method of claim 1, wherein the distillation process is carried out at a top temperature of at most 157° C.

8. The method of claim 1, wherein the distillation process is carried out at a top pressure of 0.2-0.35 bar.

9. The method of claim 1, wherein the pressure drop over the distillation column is 0.02-0.2 bar.

10. The method of claim 1, wherein at least one condenser is used in the distillation process.

11. The method of claim 1, wherein a reboiler is used in the distillation process, wherein the reboiler is operated at a pressure of 0.1-0.5 bar.

12. The method of claim 1, wherein recovering mono-ethylene glycol comprises removing mono-ethylene glycol from the distillation column at a point, which is situated below the point, wherein the mixture feed is fed into the distillation column.

13. The method of claim 12, wherein the point, wherein mono-ethylene glycol is removed from the distillation column, is situated below the lowest theoretical stage of the distillation column.

14. The method of claim 1, wherein the method comprises removing a top stream from the distillation column, wherein the top stream comprises mono-propylene glycol and an azeotrope of mono-ethylene glycol and 1,2-butylene glycol.

15. The method of claim 1, wherein the method comprises recovering mono-ethylene glycol at a concentration of at least 99.5 weight %.

* * * * *